(12) United States Patent
Gutkowski et al.

(10) Patent No.: US 7,964,178 B2
(45) Date of Patent: Jun. 21, 2011

(54) MODIFIED COLORANTS AND USES OF THE SAME

(75) Inventors: Glenn A. Gutkowski, Rahway, NJ (US); William F. Thys, Elmwood Park, NJ (US)

(73) Assignee: Sensient Colors Incorporated, St. Louis, MO (US)

( * ) Notice: Subject to any disclaimer, the term of this patent is extended or adjusted under 35 U.S.C. 154(b) by 1268 days.

(21) Appl. No.: 11/339,104

(22) Filed: Jan. 25, 2006

(65) Prior Publication Data

US 2007/0020208 A1    Jan. 25, 2007

Related U.S. Application Data (60) Provisional application No. 60/700,414, filed on Jul. 19, 2005, provisional application No. 60/700,415, filed on Jul. 19, 2005.

(51) Int. Cl.
| | |
|---|---|
| *A61K 8/87* | (2006.01) |
| *A61K 8/18* | (2006.01) |
| *A61Q 1/10* | (2006.01) |
| *A61Q 1/06* | (2006.01) |
| *A61Q 17/04* | (2006.01) |
| *A61Q 11/00* | (2006.01) |

(52) U.S. Cl. ............ 424/49; 424/59; 424/63; 424/64; 424/70.7

(58) Field of Classification Search .............. None
See application file for complete search history.

(56) References Cited

U.S. PATENT DOCUMENTS

| | | | |
|---|---|---|---|
| 4,842,848 A | 6/1989 | Saita et al. | |
| 5,302,199 A | 4/1994 | Prengel et al. | |
| 5,468,289 A | 11/1995 | Herget et al. | |
| 5,718,907 A | 2/1998 | Labarre | |
| 6,019,831 A | 2/2000 | Schmidt et al. | |
| 6,113,683 A | 9/2000 | Herren et al. | |
| 6,139,962 A | 10/2000 | Herget et al. | |
| 6,156,428 A | 12/2000 | Gibson | |
| 6,294,010 B1 | 9/2001 | Pfaff et al. | |
| 6,508,876 B1 * | 1/2003 | Bernhardt et al. | ............ 106/415 |
| 6,511,672 B2 | 1/2003 | Tan et al. | |
| 6,777,085 B1 | 8/2004 | Argoitia et al. | |
| 6,840,993 B2 | 1/2005 | Schmidt et al. | |
| 6,858,072 B1 | 2/2005 | Li et al. | |

(Continued)

FOREIGN PATENT DOCUMENTS

DE    10243438    3/2004

(Continued)

OTHER PUBLICATIONS

Pfaff, G. et al., "Angle-dependent optical effects deriving from submicron structures of films and pigments," Chemical Reviews (1999) 99:1963-1981.

(Continued)

*Primary Examiner* — Shanon A Foley (74) *Attorney, Agent, or Firm* — Michael Best & Friedrich LLP (57) ABSTRACT

Modified colorants are made from a modifying agent, such as platelet alumina, and a colorant. The colorant may be fixed to the surface of the modifying agent, optionally with a surface treatment. The colorant may not completely coat the surface of the modifying agent, and the edge of the modifying agent may be substantially free of colorant. The modified colorants may be used in cosmetic products.

22 Claims, 2 Drawing Sheets

U.S. PATENT DOCUMENTS

| | | | |
|---|---|---|---|
| 6,905,696 B2 * | 6/2005 | Marotta et al. | 424/401 |
| 2004/0166316 A1 | 8/2004 | Noguchi | |
| 2004/0244640 A1 | 12/2004 | Vogt et al. | |

FOREIGN PATENT DOCUMENTS

| | | |
|---|---|---|
| EP | 0763573 | 3/1997 |
| GB | 2268504 | 1/1994 |
| WO | WO 2004/060804 | 7/2004 |

OTHER PUBLICATIONS www.apt-powders.com/alusion.php, Advanced Nano: Products: Alusion—the soft focus powder with superior clip, adhesion (2005).

http://www.warf.ws/technologies.jsp?techfield=Materials&msnum=680&casecode=T05009US, WARF: Metal powders containing nanoscale platelet-shaped metal particles (2005).

* cited by examiner

MODIFIED COLORANTS AND USES OF THE SAME

CROSS-REFERENCE TO RELATED APPLICATIONS

This application claims priority to U.S. Provisional Application Nos. 60/700,414, filed Jul. 19, 2005, and 60/700,415 filed Jul. 19, 2005, the subject matter of each of which is hereby fully incorporated by reference.

BACKGROUND

In the cosmetics and personal care industry, pigments and traditional pearls are used to add color to a variety of products. Pigments generally have a matte appearance prior to application and also provide a matte finish after application to the skin. Traditional pearls generally have a pearlescent appearance prior to application and also provide a pearlescent appearance after application to the skin.

SUMMARY

In one aspect, the present invention provides a modified colorant having platelet alumina, a colorant and a surface treatment. The colorant may be adhered to the platelet alumina by the surface treatment.

In another aspect, the present invention provides a method of making a modified colorant by dry blending platelet alumina and a colorant to form a dry blend and adding a surface treatment to the dry blend to form the modified colorant.

In yet another aspect, the invention provides a modified colorant including platelet alumina having a surface area that is from about 5% to about 99% coated with a colorant.

In a further aspect, the invention provides a method of making a modified colorant by mixing a first slurry, dispersion or solution comprising the colorant with a second slurry comprising the platelet alumina to form a third slurry; the third slurry may be filtered to obtain the modified colorant.

In another aspect, the present invention provides a modified colorant having platelet alumina coated with a colorant. The edge of the platelet alumina may be substantially free of colorant.

In another aspect, the invention provides a method of improving the burnishing properties of a colorant, by mixing the colorant with platelet alumina and adding a surface treatment to form a modified colorant. The modified colorant may have the colorant adhered to the platelet alumina by the surface treatment. The platelet alumina may have a surface area of which about 5% to about 99% is coated with the colorant. The surface area of the platelet alumina may have an upper surface, a lower surface and an edge being substantially free of the colorant. The edge of the platelet alumina separates the upper and lower surfaces. The addition of the surface treatment to the platelet alumina and colorant may improve the burnishing properties of the colorant.

Other embodiments of the invention include cosmetic products that contain modified colorants.

DETAILED DESCRIPTION

Before any embodiments of the invention are explained in detail, it is to be understood that the invention is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The present invention is generally directed to a modified colorant comprising a colorant and a modifying agent that are combined together (e.g. dry blended) and in some embodiments, surface treated. In some embodiments, the colorant is laked or otherwise fixed to the modifying agent by mixing a solution, dispersion, slurry, or combination thereof of the colorant with the modifying agent.

As used herein, the term "colorant" generally refers to a color extender, dye, pigment, lake, toner, other agent, or a combination thereof, used to impart a color to a material. In addition, the term "colorant" can include inorganic, organic, water-soluble and water-insoluble substances.

As used herein, the term "modifying agent" can include a substrate responsible for imparting additional optical or visual properties to the material. For example, the modifying agent can include, but is not limited to, one or more metal oxides, such as aluminum oxide (alumina), zinc oxide, silicon dioxide (silica), magnesia, or a combination thereof. In some embodiments, examples of the modifying agent can include, but are not limited to, talc, mica, kaolin, bismuth oxychloride, stainless steel, graphite, platy metals such as bronze, copper and aluminum or a combination thereof. Specifically, the modifying agent can include a platelet-like metal oxide, such as platelet alumina.

As used herein, the term "platelet" generally refers to a substantially planar and flaky material that is generally not spherical. The platelets of the present invention are generally greater in width and length than in thickness. For example, suitable platelets may have an average diameter of between 1 and 20 microns, and an average thickness less than 0.5 microns. An example of a platelet alumina that can be used with present invention is ALUSION™ platelet alumina, available from Advanced Nanotechnology Limited, Welshpool, Western Australia.

As used herein, the "modified colorant" of the present invention may comprise a colorant and a modifying agent.

As used herein, the term "traditional pearl" or "synthetic pearl" generally refers to colorants based on inorganic layers (i.e., coatings) formed upon mica or glass substrates through calcination. For example, some traditional pearls include a thin layer of titanium dioxide and/or iron oxide formed on a mica platelet upon which other colorants may be deposited.

As used herein, the term "payoff" generally refers to the appearance of a cosmetic or personal care product when it is applied to or spread onto a surface, such as the skin. For example, the payoff of an eye shadow can have a varying color, texture, consistency, or finish.

As used herein, the term "finish" generally refers to the luster, shininess, or image reflection of a material. For example, a material can have a matte finish (i.e., a low luster or shininess), a glossy or reflective finish (i.e., a high luster or shine), and combinations thereof.

As used herein, the term "pearlescent" generally describes a material that exhibits a spectrum of colors resulting from light refraction instead of pigmentation. In other words, a "pearlescent" material exhibits colors depending on the angles of illumination and viewing. A "pearlescent" material generally appears to have a glossy finish, rather than a matte finish.

As used herein, the term "masstone" generally refers to the appearance of a thick layer of a colorant either dry or when incorporated into a vehicle such as water or castor oil. For example, the masstone of a cosmetic product can generally refer to the appearance of the product prior to application of the product.

As used herein, the term "burnish" generally refers to a change of gloss or finish induced by friction between two or more surfaces, which may align particles with one another and in parallel with the surface to which they are being applied. For example, "burnishing" a powder can include, but is not limited to, rubbing or brushing the powder onto the skin, rubbing the powder between two or more fingers, or a combination thereof.

As used herein, the term "lake" generally refers to a colorant that is prepared by precipitating a soluble dye onto an insoluble reactive or adsorptive substratum or diluent.

In some embodiments, the present invention is generally directed to a modified colorant comprising a colorant and a modifying agent. The colorant and the modifying agent may be dry blended together and surface treated to lock, physically fix or adhere the colorant and the modifying agent together, either directly or indirectly, in a loose association. In some embodiments, the colorant and the modifying agent may each be combined with a liquid such as water to form a slurry, dispersion or solution, and then the slurries, dispersions or solutions can be combined together. The resulting slurry, dispersion or solution can be filtered and dried to form a modified colorant comprising a modifying agent coated with a colorant. In some embodiments, the modified colorant formed according to the process of the present invention may include a lake.

The type of bonding that can occur between the colorant and the modifying agent of the modified colorant can vary, depending on the relative chemistry of the colorant and the modifying agent. For example, in some embodiments, a variety of strong chemical bonds and/ or weak chemical bonds may form between the colorant and the modifying agent. As used herein, "strong chemical bonds" may include covalent bonds, ionic bonds, or a combination thereof, and "weak chemical bonds" may include electrostatic interactions, dipole-dipole interactions such as hydrogen bonds, charge-transfer complexes, hydrophobic interactions, and van der Waals (or London) dispersion forces, or combinations thereof. In one aspect of the invention, a colorant molecule that is attached to the modifying agent by weak chemical bonds is considered to be physically fixed to the modifying agent. It is envisaged that at least about 30%, at least about 40%, at least about 50%, at least about 60%, at least about 70%, at least about 80%, at least about 90%, at least about 95% or at least about 99% of the colorant molecules may be physically fixed or physically bonded to the modifying agent entirely by physical bonds.

In some embodiments, the modified colorant can be surface treated with a variety of surface treatment chemicals, including, but not limited to, one or more of aluminum laurate, aluminum stearate, amino acids, chitin, collagen, fluorochemicals, lecithins, metal soaps, natural waxes, polyacrylates, polyethylenes, silicones (e.g., dimethicone copolyol, such as PEG 12M, dimethicone copolyol, dimethicone, methicone), silanes (e.g., octytriethoxysilane, triethoxycaprylylsilane, trimethoxycaprylylsilane), titanatate esters, urethanes, perfluoropolymethylisopropyl ether, styrene acrylates copolymer, magnesium myristate, lauroyl lysine, and combinations thereof.

In one embodiment, the surface treatment adheres the colorant molecules to the modifying agent either directly or indirectly. As used herein, the term "adhere" generally refers to the colorant being fixed to the modifying agent by adhesive forces between the surface treatment and the modifying agent, and the surface treatment and the colorant. The adhesive forces may include bonds that mechanically lock the surfaces together, strong chemical bonds (such as covalent bonds), weak chemical bonds and combinations thereof. In some embodiments, the adhesive forces maintain the colorant in a loose association with the modifying agent. It is envisaged that at least about 30%, at least about 40%, at least about 50%, at least about 60%, at least about 70%, at least about 80%, at least about 90%, at least about 95% or at least about 99% of the colorant molecules may be adhered to the modifying agent entirely by adhesive bonds. Modified colorants comprising a colorant, such as a pigment, adhered with a surface treatment to a modifying agent, such as platelet alumina are more homogeneous than those produced from a dry blend. The modified colorants of the present invention tend not to segregate, for example during shipping, and can be applied more evenly.

The final composition of the modified colorant includes colorant molecules partially coated on the modifying agent. A full coating is generally not formed, and the modifying agent may or may not be fully encapsulated by the colorant. In some embodiments, the modifying agent, such as a flake or platelet, comprises an upper and a lower surface separated by an edge, the edge being narrower than the average diameter or dimensions of the upper and lower surfaces, and the colorant coats the upper and lower surfaces of the modifying agent, but the edge of the modifying agent is substantially free of colorant. As used herein, the term "substantially free of colorant" generally means that at least 90% of the total surface area of the edge of the modifying agent has no colorant adhered or bonded to it. Modifying agents having an edge substantially free of colorant show a reduced drag and have an improved feel when burnished, or rubbed against the skin or other surface.

Figure 1:
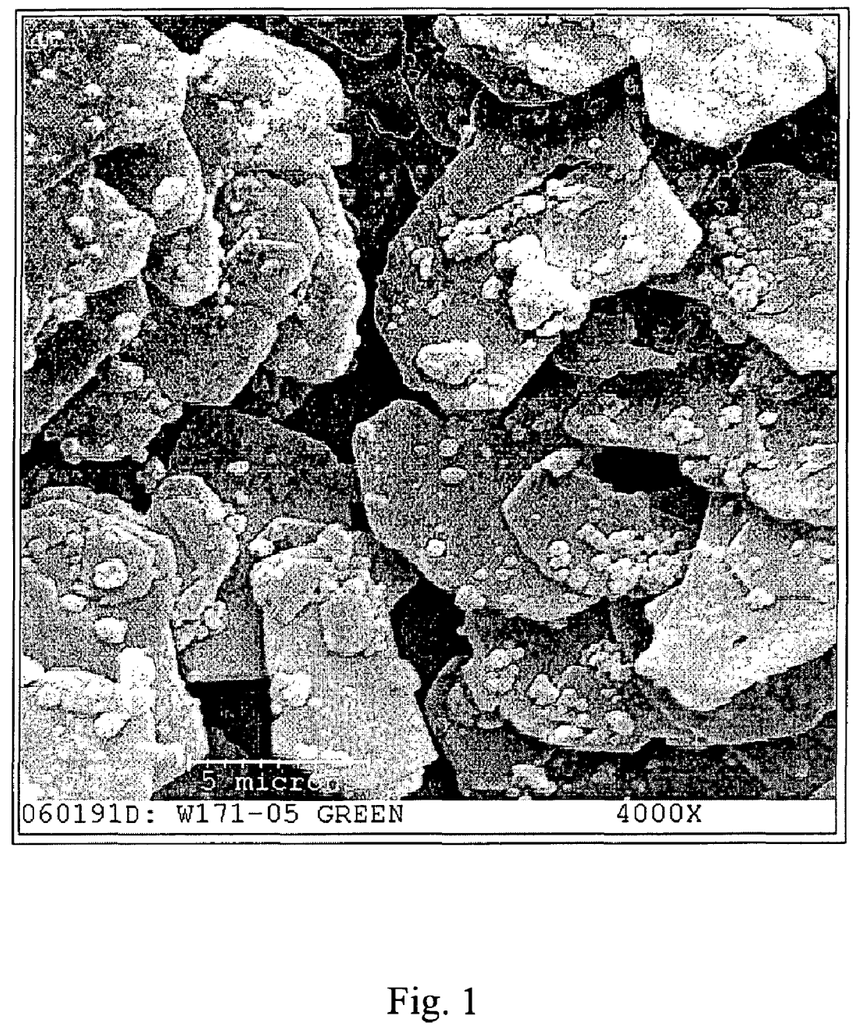
FIG. 1. is a photograph showing a scanning electron micrograph showing one embodiment of the invention: a modified colorant comprising platelet alumina to which chromium oxide is adhered using a surface treatment. The chromium oxide is seen as agglomerates on the platelet alumina.
Figure 2:
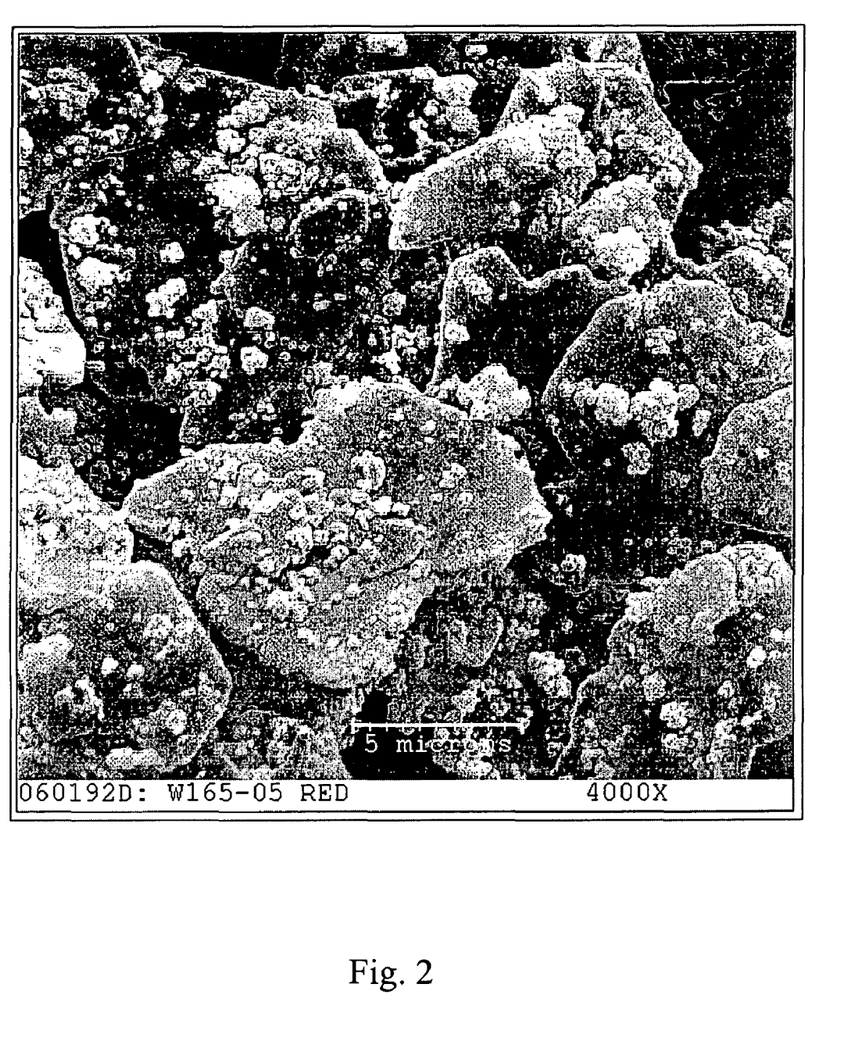
FIG. 2. is a photograph showing a scanning electron micrograph showing one embodiment of the invention: a modified colorant comprising platelet alumina to which red iron oxide is adhered using a surface treatment. The red iron oxide is seen as agglomerates on the platelet alumina.

FIG. 1 is a scanning electron micrograph of a modified colorant and shows a modifying agent (platelet alumina) partially coated with colorant (chromium oxide), wherein the edges of the modifying agent are substantially free of colorant. The chromium oxide was added to platelet alumina at a weight of 20% of the total combined weight of the colorant and the platelet alumina. In FIG. 1, agglomerates of the chromium oxide were adhered to the platelet alumina using a surface treatment. FIG. 2 is a scanning electron micrograph of a modified colorant and shows a modifying agent (platelet alumina) partially coated with colorant (red iron oxide), wherein the edges of the modifying agent are substantially free of colorant. The red iron oxide was added to platelet alumina at a weight of 20% of the total combined weight of the colorant and the platelet alumina. In FIG. 2, agglomerates of the red iron oxide were adhered to the platelet alumina using a surface treatment. In some embodiments, the modifying agent is at least partially exposed, or covered by the surface treatment, but is not fully covered by the colorant. For example, in some embodiments, the colorant may cover or coat more than about 1%, 3%, 5%, 10%, 15%, 20%, 30%, 40% or 50% of the total surface area of the modifying agent and less than about 99%, 95%, 90%, 85%, 80%, 75%, 65%, 50%, 40%, 30%, 25%, 20%, 15% or 10%, of the total surface area of the modifying agent. Modified colorants that comprise modifying agents, such as platelet alumina, not fully covered by the colorant have more surfaces for light to reflect off and burnish more easily compared with fully covered modifying agents. In contrast, modified colorants that are fully or completely coated with colorant tend to be non-reflective and exhibit less burnishing. Improved light reflection and improved burnishing are properties that can be desirable to end users of the modified colorants, particularly those in the cosmetic industry.

In some embodiments, the appearance of the modified colorant of the present invention as a loose or pressed powder includes a substantially matte appearance. However, when the modified colorant is burnished, it exhibits a reflective finish, and particularly, a metallic sheen. In embodiments including platelet alumina, it is hypothesized that the metallic effect results after burnishing because the partial layer of colorant is rubbed to a thinner layer (e.g., a single layer) that is more translucent than a thicker layer, and which allows light to reflect off of the substantially planar surfaces of the platelet alumina.

For some embodiments, the modified colorant of the present invention can be formed by the following process:

(1) Dry blending a colorant with one or more modifying agents at ambient temperature and pressure (i.e., about 25 degrees C. and about 1 atm) to form a dry blend.

(2) Adding a surface treatment to the dry blend to form a mixture.

(3) Mixing the mixture at ambient temperature and pressure.

In some embodiments, steps 1 and 2 above are performed simultaneously. In other words, the colorant, modifying agent and surface treatment can all be combined together in a first step, and then mixed.

In step 2 above, the surface treatment can be added to substantially hold or adhere the colorant and the modifying agent in association with one another.

In step 3 above, the mixture can be mixed for at least about 30 seconds, particularly, at least about 5 minutes, and more particularly, at least about 12 minutes. In some embodiments, the mixture is mixed for less than about 30 minutes, particularly, less than about 25 minutes, and more particularly, less than about 20 minutes.

For some embodiments, the modified colorant of the present invention can be formed by the following process:

(A) Combining a colorant with a liquid, (e.g., water, such as tap water) to form a first slurry, dispersion or solution.

(B) Combining a modifying agent with a liquid, (e.g., water, such as tap water) to form a second slurry or dispersion.

(C) Combining the first slurry and the second slurry to form a third slurry or dispersion. In some embodiments, the first slurry is added to the second slurry to form the third slurry, and in some embodiments, the second slurry is added to the first slurry to form the third slurry.

(D) Mixing the third slurry.

(E) Filtering the third slurry to form recovered solids.

(F) Drying the recovered solids.

(G) In embodiments employing a surface treatment, the surface treatment can be accomplished by the following process:

(i) Adding one or more of the surface treatment chemicals to the modified colorant to form a mixture.

(ii) Mixing the mixture at ambient temperature and pressure.

In step A, the colorant and water can be mixed using a variety of mixing devices. The mixing devices can include, but are not limited to, magnetic stirrers, blenders, magnet stirrers equipped with a baffle, agitators-in-tank, or combinations thereof. The colorant and water can be mixed for at least about 30 minutes, particularly, at least about 45 minutes, and more particularly, at least about 1 hour. In some embodiments, the colorant and the water can be mixed for less than about 25 hours, particularly, less than about 3 hours, and more particularly, less than about 2 hours.

In step B, the modifying agent and water can be mixed using a variety of mixing devices. The mixing devices can include, but are not limited to, magnetic stirrers, blenders, magnet stirrers equipped with a baffle, agitators-in-tank, or combinations thereof. The modifying agent and the water can be mixed for at least about 30 minutes, particularly, at least about 45 minutes, and more particularly, at least about 1 hour. In some embodiments, the colorant and the water can be mixed for less than about 25 hours, particularly, less than about 3 hours, and more particularly, less than about 2 hours.

In step B, other ingredients may be added to the second slurry, including, but not limited to, metallic salts, acids, bases, or combinations thereof. In some embodiments, the pH of the second slurry can be monitored, buffered or adjusted.

In step D, the third slurry can be mixed using a variety of mixing devices. The mixing devices can include, but are not limited to, magnetic stirrers, blenders, magnet stirrers equipped with a baffle, agitators-in-tank, or combinations thereof. The third slurry can be mixed for at least about 30 minutes, particularly, at least about 45 minutes, and more particularly, at least about 1 hour. In some embodiments, the third slurry can be mixed for less than about 25 hours, particularly, less than about 3 hours, and more particularly, less than about 2 hours.

In step E, the third slurry can be filtered using at least one of a filter press, a Buchner filter, reverse osmosis, vacuum filtration, etc., and combinations thereof.

In step F, the recovered solids can be dried by heating (e.g., in an oven) at a temperature of at least about 140 degrees F., particularly, at least about 150 degrees F., and more particularly, at least about 160 degrees F. In some embodiments, the recovered solids can be dried by heating at a temperature of less than about 210 degrees F., particularly, less than about 190 degrees F., and more particularly, less than about 180 degrees F. The drying/heating step can occur for a period of at least about 2 hours, particularly, at least about 10 hours, and more particularly, at least about 25 hours. In some embodiments, the drying/heating step can occur for less than about 45 hours, particularly, less than about 40 hours, and more particularly, less than about 36 hours.

The first slurry is not necessarily formed prior to the formation of the second slurry. The terms "first slurry" and "second slurry" are not necessarily used to indicate order. In some embodiments, steps A and B occur simultaneously. In some embodiments, one of the first slurry or the second slurry is formed before the other.

In some embodiments of the present invention, the recovered solids formed in step E are surface treated by one of the methods described above.

The third slurry can be tested for color bleed, to determine the strength of adhesion of the colorant to the modifying agent, and the pH of the third slurry can be tested. In some embodiments, the pH of the third slurry is at least about 2, particularly, at least about 4, and more particularly, at least about 6. In some embodiments, the pH of the third slurry is less than about 13, particularly, less than about 11, and more particularly, less than about 9.

In step B of the surface treatment process, the mixture can be mixed for at least about 30 seconds, particularly, at least about 5 minutes, and more particularly, at least about 12 minutes. In some embodiments, the mixture is mixed for less than about 30 minutes, particularly, less than about 25 minutes, and more particularly, less than about 20 minutes.

A variety of weight percentages of colorant to water can be used with the present invention to form the first slurry, including a weight percentage of at least about 0.5%, particularly, at least about 1%, and more particularly, at least about 2%. In some embodiments, the weight percentages of colorant to water is less than about 10%, particularly, less than about 9%, and more particularly, less than about 7%.

A variety of weight percentages of modifying agent to water can be used with the present invention to form the second slurry, including a weight percentage of at least about 1%, particularly, at least about 2%, and more particularly, at least about 5%. In some embodiments, the weight percentages of modifying agent to water is less than about 35%, particularly, less than about 30%, and more particularly, less than about 25%.

In some embodiments, one or more of the colorant and the surface treatment is hydrated. In some embodiments, water is added to the dry blend and/or to the mixture.

In embodiments employing a surface treatment in which water is present, the mixture can be dried after being mixed at ambient temperature and pressure. The mixture can be dried by heating (e.g., in an oven) at a temperature of at least about 70 degrees C., particularly, at least about 75 degrees C., and more particularly, at least about 80 degrees C. The mixture can also be heated to a temperature of less than about 110 degrees C., particularly, less than about 100 degrees C., more particularly less than about 95 degrees C. and even more particularly, less than about 90 degrees C. The mixture can be heated for a period of time of at least about 1 hour, particularly, at least about 1.5 hours, and more particularly, at least about 2 hours. In some embodiments, the mixture can be heated for less than about 48 hours, particularly, less than about 36 hours, and more particularly, less than about 18 hours.

A variety of weight percentages of colorant to modifying agent can be used with the present invention. For some embodiments, the weight percentage of colorant to modifying agent can be at least about 3%, 5%, 6%, 10%, 11%, 15%, 20%, 25%, 30%, 35%, 40%, 45% or 50% of colorant to modifying agent. In some embodiments, the weight percentage of colorant to modifying agent is less than about 97%, 90%, 85%, 80%, 75%, 70%, 65%, 60%, 55%, 50%, 45%, 40%, 35%, 30%, 25% or 20%.

A variety of weight percentages of surface treatment to dry blend can be used with the present invention, including a weight percentage of at least about 0.5%, particularly, at least about 0.75%, and more particularly, at least about 1%. In some embodiments, the weight percentage of surface treatment to dry blend is less than about 30%, particularly, less than about 25%, and more particularly, less than about 20%.

Examples of pigments that can be used include both inorganic and organic pigments. Inorganic pigments can include, but are not limited to, at least one of iron oxides (e.g., yellow, red, umber, brown, and black), ferric ferrocyanide (e.g., blue), manganese violet, ultramarine blue, talc, zeolite, kaolin, titanium dioxide (e.g., white), zinc oxide, chromium oxide, chromium hydroxide, and combinations thereof. Organic pigments can include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof. Examples of dyes, toners and lakes that can be used include, but are not limited to, at least one of primary FD&C or D&C Lakes and blends thereof, such as FD&C Yellow 5, FD&C Yellow 6, D&C Yellow 10, D&C Red 6, D&C Red 7, D&C Red 21, D&C Red 27, D&C Red 28, D&C Red 30, D&C Red 33, D&C Red 36, D&C Red 40, D&C Green 6, carmine, and D&C Blue 1, FD&C Blue 1, bromo dyes, fluorescein dyes, and combinations thereof.

The modified colorant formed by the above process can be lipophilic, hydrophobic, hydrophilic, or a combination thereof, depending on the surface treatment. Hydrophobicity can be determined by sprinkling dry modified colorant over still, deionized water, and observing the modified colorant after about 1 hour. If the modified colorant remains on the surface of the water, it is substantially hydrophobic. In addition, if the modified colorant overcomes the surface tension of the water and penetrates the surface of the water, but does not disperse or dissolve, the modified colorant is substantially hydrophobic. On the other hand, if the modified colorant disperses and/or dissolves in the water, the modified colorant is substantially hydrophilic. The above tests are all visual. As understood by those of ordinary skill in the art, other tests exist to determine whether the final powder is hydrophilic or lipophilic. Such tests can be used without departing from the spirit and scope of the present invention.

The modified colorant of the present invention can be used in a variety of applications, including, but not limited to, at least one of cosmetic products, personal care products, hair care products, paints, inks, plastics, leather and other surface treatments, other applications in the automobile industry, other applications in the printing industry, and combinations thereof.

Cosmetic products can include, but are not limited to, mascaras, pressed powder make-ups (e.g., eye shadows, cheek rouge and facial powders), liquid make-ups (e.g., eye shadows, foundations, cheek rouge, blushes, lip liners, eye liners and nail enamel), lipsticks and other cosmetics made using silicones, or combinations thereof. Personal care products can include, but are not limited to, lotions, creams, gels, toothpastes or combinations thereof.

The modified colorant can be combined with a variety of other components to form one or more of the products listed above. Additional components may include, but are not limited to, at least one of other colorants, water soluble sunscreens (such as Eusolex 232); oil soluble sunscreens (such as octyl methoxycinnamate); and organic sunscreens (such as camphor derivatives, cinnamates, salicylates, benzophenones, triazines, PABA derivatives, diphenylacrylate derivatives, and dibenzoylmethane derivatives.); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents, such as cholesterol; cationic polymers (such as Polyquaternium 10); anionic polymers (such as xanthan gum); pigment wetting agents, such as Arlacel™ P100 (polyhydroxystearic acid), or Emerest™ 2452 (Polyglyceryl-3 Diisostearate); vitamins (such as tocopherol); or combinations thereof.

Examples of other components that can be combined with the modified colorants of the present invention to form one or more of the products listed above include, but are not limited to, fats and oils, waxes, surfactants, oxidation inhibitors, UV absorbers, vitamins, hormones, squalenes, liquid paraffins, fatty acids, bees wax, myristyl myristate and other esters, acetone, toluene, butyl acetate, acetic ester and other solvents; antioxidants, antiseptic agents, polyhydric alcohols, perfumes, or combinations thereof.

Examples of other colorants that can be used in combination with the modified colorants of the present invention to form a variety of products, include, but are not limited to, titanium dioxide; calcium carbonate; clay; talc; barium sulfate; white carbon; chromium oxide; zinc oxide; zinc sulfide; zinc powder; metal powder pigments; iron black; yellow iron oxide; red iron oxide; chrome yellow; carbon black; molybdate orange; Prussian Blue; ultramarine blue; cadmium type pigments; fluorescent pigments; soluble azo dyes; insoluble azo dyes; condensed azo dyes; phthalocyanine pigments; condensed polycyclic pigments; composite oxide pigments; graphite; mica (such as, muscovite, phlogopite, synthetic mica, and fluorine tetra silicon mica); metal oxide coated mica (such as titanium oxide coated mica, titanium dioxide coated mica, (hydrated) iron oxide coated mica, mica coated with iron oxides and titanium oxides, mica coated with lower ordered titanium oxides); metal oxide coated graphite (such as titanium dioxide coated graphite); thin platelet-like alumina; metal oxide coated thin platelet-like alumina (such as titanium dioxide coated thin platelet-like alumina, iron oxide coated thin platelet-like alumina, $Fe_2O_3$ coated thin platelet-like alumina, $Fe_3O_4$ coated thin platelet-like alumina, interference color metal oxide coated thin platelet-like alumina); metal flake pigments (such as aluminum flakes, colored aluminum flakes, stainless steel flakes, titanium flakes); anti-corrosive metal flakes (such as base flakes of aluminum flake substrates); metal oxide coated metal flakes (such as titanium oxide or iron oxide coated aluminum flakes); MIO; metal oxide coated MIO; metal oxide coated silica flakes and metal oxide coated glass flakes called optical effect pigments (effect pigments); photochromic pigments; thermochromic pigments; holographic pigments; sericite; magnesium carbonate; silica; zeolite; hydroxyapatite; chromium oxide; cobalt titanate; glass beads; nylon beads; silicone beads; red nos. 2, 3, 102, 104, 105, 106, 201, 202, 203, 204, 205, 206, 207, 208, 213, 214, 215, 218, 219, 220, 221, 223, 225, 226, 227, 228, 230-1, 230-2, 231, 232, 405; yellow nos. 4, 5, 201, 202-1, 202-2, 203, 204, 205, 401, 402, 403, 404, 405, 406, 407; green nos. 3, 201, 202, 204, 205, 401, 402; blue nos. 1, 2, 201, 202, 203, 204, 205, 403, 404; orange nos. 201, 203, 204, 205, 206, 207, 401, 402, 403; brown no. 201; violet nos. 201, 401; black no. 401; salol yellow; carmine; beta-carotin; hibiscus color; capsaicin; carminic acid; laccaic acid; gurcumin; riboflavin; shikonin; or a combination thereof.

Other products may comprise the modified colorant of the present invention combined with one or more active components. Examples of active components can include, but not limited to, those that improve or eradicate age spots, keratoses and wrinkles, anti-cavity ingredients for oral care and toothpaste products, such as fluoride, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, sunscreens, hormones, or combinations thereof. Examples of active compounds can further include, but are not limited to, retinoids, such as retinol, and esters, acids, and aldehydes thereof; ascorbic acid, and esters and metal salts thereof; tocopherol and esters and amide derivatives thereof; shark cartilage; milk proteins; alpha- or beta-hydroxy acids; DHEA and derivatives thereof; topical cardiovascular agents; or combinations thereof. Examples of active compounds can also include, but are not limited to, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone diproprionate, triaminolone acetonide, fluocinonide, clobetasol, proprionate, benzoyl peroxide, crotamiton, propranolol, promethazine, or a combination thereof.

Various features and aspects of the invention are set forth in the following examples.

EXAMPLE 1

Yellow Iron Oxide Dry Blended with Platelet Alumina 24 g of moist yellow iron oxide (Unipure LC 182, available from Sensient), 96 g of ALUSION™ platelet alumina, and 2 g of octyltriethoxysilane were combined and mixed for about 30 seconds to form a mixture. The mixture was heated overnight in an oven at about 80 degrees C. As determined by observation, the payoff of the modified colorant had a slight glossy finish. The percentage loss on drying was about 0.65%, and the modified colorant was hydrophobic.

EXAMPLE 2

Red Iron Oxide Dry Blended with Platelet Alumina 24 g of moist red iron oxide (Unipure LC 380 from Sensient), 96 g of ALUSION™ platelet alumina, and 2 g of octyltriethoxysilane (INCI name triethoxycaprylylsilane) is combined and mixed for about 30 seconds. The mixture is heated overnight in an oven at about 80 degrees C.

EXAMPLE 3

Black Iron Oxide Dry Blended with Platelet Alumina 24 g of moist black iron oxide (Unipure LC 989 from Sensient), 96 g of ALUSION™ platelet alumina, and 2 g of octyltriethoxysilane (International Nomenclature of Cosmetic Ingredients (INCI) name: triethoxycaprylylsilane) is combined and mixed for about 30 seconds. The mixture is heated overnight in an oven at about 80 degrees C.

EXAMPLE 4

Titanium Dioxide Dry Blended with Platelet Alumina 24 g of moist titanium dioxide (Unipure LC 981 from Sensient), 96 g of ALUSION™ platelet alumina, and 2 g of octyltriethoxysilane (INCI name triethoxycaprylylsilane) is combined and mixed for about 30 seconds. The mixture is heated overnight in an oven at about 80 degrees C.

EXAMPLE 5

Chromium Hydroxide Dry Blended with Platelet Alumina 24 g of moist chromium hydroxide (Unipure LC 788 from Sensient), 96 g of ALUSION™ platelet alumina, and 2 g of octyltriethoxysilane (INCI name triethoxycaprylylsilane) is combined and mixed for about 30 seconds. The mixture is heated overnight in an oven at about 80 degrees C.

EXAMPLE 6

D&C Red 6 Dry Blended with Platelet Alumina 18 g of moist D&C Red 6, 102 g of ALUSION™ platelet alumina, and 2 g of octyltriethoxysilane (INCI name: triethoxycaprylylsilane) were combined and mixed for about 30 seconds. The mixture was heated overnight in an oven at about 80 degrees C. As determined by observation, the resulting modified colorant had an intense red-orange masstone, with a glossy finish. The percentage loss on drying was about 1.0%, and the modified colorant was hydrophobic.

EXAMPLE 7

D&C Red 7 Dry Blended with Platelet Alumina 18 g of moist D&C Red 7, 102 g of ALUSION™ platelet alumina, and 2 g of octyltriethoxysilane (INCI name: triethoxycaprylylsilane) is combined and mixed for about 30 seconds. The mixture is heated overnight in an oven at about 80 degrees C.

EXAMPLE 8

Carbon Black Dry Blended with Platelet Alumina 20 g of moist carbon black, 79 g of ALUSION™ platelet alumina, and 2 g of octyltriethoxysilane (INCI name: triethoxycaprylylsilane) were combined and mixed for about 30 seconds. The mixture was heated overnight in an oven at about 80 degrees C. As determined by observation, the resulting modified colorant had a black, matte masstone, with a metallic sheen on application to the skin. The percentage loss on drying was about 0.6%, and the modified colorant was hydrophobic.

EXAMPLE 9

Carbon Black Dry Blended with Platelet Alumina 20 g of moist carbon black, 79 g of ALUSION™ platelet alumina, and 2 g of PEG 12M Dimethicone Copolyol is combined and mixed for about 30 seconds. The mixture is heated overnight in an oven at about 80 degrees C. The resulting modified colorant should have a black masstone, with a metallic sheen on application to the skin.

EXAMPLE 10

Dispersion of Carbon Black Dry Blended with Platelet Alumina

A modified colorant formed according to Example 9 is dispersed into propylene glycol using a three-roll mill until the final colorant content is about 60%. The resulting dispersion is further incorporated into a mascara formulation.

EXAMPLE 11

Water-Resistant Mascara Including Modified Colorants

| MATERIALS: | % W/W |
|---|---|
| Phase A | |
| Pure Water | 44.00 |
| COVACRYL RH | 0.10 |
| FUCOMER | 1.00 |
| Methylparaben | 0.30 |
| Phase B | |
| MODIFIED COLORANT FORMED ACCORDING TO EXAMPLE 3 | 6.00 |
| MODIFIED COLORANT FORMED ACCORDING TO EXAMPLE 8 | 6.00 |
| COVABEAD PMMA | 2.00 |
| Phase C | |
| BASE O/W 097 | 6.50 |
| Candellila | 2.50 |
| COVALIP 99 | 1.50 |
| SILAMER | 1.30 |
| Propylparaben | 0.30 |
| Phase D | |
| FIBERLON 102 DC B2 | 0.30 |
| Phase E | |
| Pure Water | 10.00 |
| PPG-17/IPDI/DMPA | 3.00 |
| COVACRYL E14 | 11.00 |
| COVACRYL A15 | 3.50 |

METHODS:
1. Phase A: Heat water in main vessel to 70° C., add remaining components one by one using a propeller mixer until dissolved.
2. Slowly add Phase B to A, homogenize under high speed mixer until a good dispersion of the color is achieved. Maintain temperature at 70° C.
3. Dissolved Phase C at 80° C. until homogeneous and maintain at temperature. When ready, add Phase C to main vessel slowly blending with a propeller blade mixer for 15 minutes at 80° C. Add Phase D and mix until homogenous.
4. Cool down main vessel to 40° C. Add premixed Phase E slowly to main vessel while stirring, maintain at 40° C. Cool to appropriate pouring temperature.
Note: pH = 7.7 (5% mascara in water)

| TRADEMARKED NAMES; AVAILABLE FROM SENSIENT LCW | INCI Name | FUNCTION |
|---|---|---|
| COVACRYL RH | Sodium polyacrylate | Water soluble thickener |
| FUCOMER | Algae extract | Skin and hair moisturizer |
| MODIFIED COLORANT FORMED ACCORDING TO EXAMPLE 3 | CI 77499 (and) Alumina (and) Triethoxycaprylylsilane | Hydrophobic modified colorant |

| TRADEMARKED NAMES; AVAILABLE FROM SENSIENT LCW | INCI Name | FUNCTION |
|---|---|---|
| MODIFIED COLORANT FORMED ACCORDING TO EXAMPLE 8 | CI 77266/D&C Black 2 (and) Alumina (and) Nylon 6 (and) Triethoxycaprylylsilane | Lengthens and volume up eyelashes; modified colorant |
| BASE O/W 097 | Ceteareth 25 (and) PEG-2 stearate (and) Paraffinum liquidum (and) Hydrogenated coconut oil (and) Cetyl alcohol (and) Sodium stearate | Self emulsifying and emollient base |
| SILAMER | Phenyl trimethicone (and) Cetyl PEG/PPG-10/1 Dimethicone (and) Polyglyceryl-2-isostearate (and) Hexyl laurate | Self emulsifying base |
| FIBERLON 102 DC B2 | Nylon 6 (and) CI 77266/D&C Black 2 | Lengthens and volume-up eyelashes |
| COVARCYL E14 & A15 | Acrylates copolymer | Film former |
| COVABEAD PMMA | Polymethylmethacrylate | Increase smoothness |
| COVALIP 99 | Ozokerite (and) Carnauba (and) Candelilla Cera (and) Paraffin (and) Ricinus communis (and) Butyl Stearate (and) Isopropyl palmitate (and) Paraffinum liquidum (and) Ethylene/VA Copolymer (and) Propylparaben | Provides gloss, long wear and good-pay-off |

EXAMPLE 12

Non Transfer Water-Based Foundation Including Modified Colorants

| MATERIALS: | % W/W |
|---|---|
| Phase A | |
| BASE RW 135 | 15.00 |
| DC 200 (350 CS) | 1.50 |
| Phase B | |
| Pure water | 42.10 |
| Triethanolamine (85%) | 0.45 |
| THICKAGENT LC | 0.45 |
| Phase C | |
| Phenonip | 0.50 |
| Phase D | |
| MODIFIED COLORANT FORMED ACCORDING TO EXAMPLE 4 | 6.30 |
| MODIFIED COLORANT FORMED ACCORDING TO EXAMPLE 2 | 0.60 |
| MODIFIED COLORANT FORMED ACCORDING TO EXAMPLE 1 | 0.90 |
| MODIFIED COLORANT FORMED ACCORDING TO EXAMPLE 3 | 0.20 |
| Phase E | |
| COVACRYL E 14 | 10.00 |
| COVACRYL A 15 | 20.00 |
| COVABEAD PMMA | 2.00 |

METHODS:
1. In a clean stainless tank, heat Phase A to 75° C. with slow stirring.
2. In a separate vessel, disperse well Thickagent LC in water to make a homogenous gel. Add then triethanolamine and heat to about 75° C.
3. Add Phase B to A with moderate agitation. Keep on stirring until the product is homogenous.
4. Add Phase C at 55° C.
5. Phase D: Disperse colorants in part of base using a three roll mill before adding to the bulk.
6. Add then Covacryl E14 and Covacryl A 15, one after another while stirring then add COVABEAD PMMA.
7. Keep on stirring until the product is homogenous and cool. Fill in suitable containers.

| TRADEMARKED NAMES; AVAILABLE FROM SENSIENT LCW | INCI Name | Function |
|---|---|---|
| BASE RW 135 | Synthetic beeswax (and) Carnauba (and) Stearic acid 9and) Ceteareth 25 (and) PEG-2 stearate (and) Paraffinum liquidum (and) Hydrogenated coconut oil (and) Cethyl alcohol | Provides texture |
| THICKAGENT LC | Xanthan gum (and) Hectorite (and) Cellulose | Thickening agent |
| MODIFIED COLORANT FORMED ACCORDING TO EXAMPLE 4 | CI 77891 (and) Alumina (and) Triethoxycaprylylsilane | Modified Colorant |
| MODIFIED COLORANT FORMED ACCORDING TO EXAMPLE 2 | CI 77491 (and) Alumina (and) Triethoxycaprylylsilane | Modified Colorant |
| MODIFIED COLORANT FORMED ACCORDING TO EXAMPLE 1 | CI 77492 (and) Alumina (and) Triethoxycaprylylsilane | Modified Colorant |
| MODIFIED COLORANT FORMED ACCORDING TO EXAMPLE 3 | CI 77499 (and) Alumina (and) Triethoxycaprylylsilane | Modified Colorant |
| COVABEAD PMMA | Polymethylmethacrylate | Increases smoothness |
| COVACRYL E 14 | Acrylates copolymer | Film former |
| COVACRYL A 15 | Acrylates copolymer | Film former |

EXAMPLE 13

Water-Soluble Fluid Foundation Including Modified Colorants

| MATERIALS: | % W/W |
|---|---|
| Phase A | |
| SILAMER | 15.00 |
| Cetyl Dimethicone | 1.90 |
| COVABEES S99 | 0.65 |
| Hydrogenated Castor oil (castor wax) | 0.30 |
| Hexyl Laurate | 2.70 |
| Phase B | |
| MODIFIED COLORANT FORMED ACCORDING TO EXAMPLE 4 | 4.95 |
| MODIFIED COLORANT FORMED ACCORDING TO EXAMPLE 3 | 0.20 |
| MODIFIED COLORANT FORMED ACCORDING TO EXAMPLE 1 | 0.90 |
| MODIFIED COLORANT FORMED ACCORDING TO EXAMPLE 2 | 0.50 |
| LUMIRAL | 2.50 |
| CM 111 AS | 6.00 |
| Phase C | |
| Dow Corning 245 | 10.00 |
| Phase D | |
| Pure Water | 47.00 |
| Polyglycerol—3 Laurate | 0.40 |
| NaCl | 0.60 |
| Propylene Glycol | 6.00 |
| Preservative | 0.40 |
| | 100.00% |

METHODS:
1. Combine Phase A and heat, mix to 80° C.
2. Disperse Phase B using a blender.
3. Add Phase B to A. Mix and homogenize for several minutes using a Turrax homogenizer.
4. Add Phase C, mix for 5 minutes and then add Phase D.
5. Cool down the batch, put into an appropriate container.

EXAMPLE 14

Transparent Soft Two-Way Cake Including Modified Colorants

| MATERIALS: | % W/W |
|---|---|
| Phase A | |
| CM 111 | 57.70 |
| MICA 8 AS | 19.20 |
| Phase B | |
| MODIFIED COLORANT FORMED ACCORDING TO EXAMPLE 8 | 1.90 |
| MODIFIED COLORANT FORMED ACCORDING TO EXAMPLE 4 | 1.90 |
| MODIFIED COLORANT FORMED ACCORDING TO EXAMPLE 2 | 9.60 |
| MODIFIED COLORANT FORMED ACCORDING TO EXAMPLE 1 | 5.80 |
| Phase C | |
| COVAPRESS TW 966 | 3.90 |

METHODS:
1. Mix all the ingredients of Phase A.
2. Mix powder base and colorants then add binder COVAPRESS TW 966 and mix during 30 seconds with a "coffee miller." Compact into suitable godets.

Remark: octyltriethoxysilane (INCI name: triethoxycaprylylsilane) treatment decreases mixing time.

| TRADEMARKED NAMES; AVAILABLE FROM SENSIENT LCW | INCI NAME | Function |
|---|---|---|
| SILAMER | Phenyl Trimethicone (and) Cetyl PEG/PPG-10/1 Dimethicone (and) Polyglyceryl-2-isosteartae (and) Hexyl Laurate | Non-ionic self emulsifying base |
| COVABEES S 99 | Synthetic beeswax | High melting point wax |
| MODIFIED COLORANT FORMED ACCORDING TO EXAMPLE 4 | CI 77891 (and) Alumina (and) Triethoxycaprylylsilane | Modified colorant |
| MODIFIED COLORANT FORMED ACCORDING TO EXAMPLE 3 | CI 77499 (and) Alumina (and) Triethoxycaprylylsilane | Modified colorant |
| MODIFIED COLORANT FORMED ACCORDING TO EXAMPLE 2 | CI 77491 (and) Alumina (and) Triethoxycaprylylsilane | Modified colorant |
| MODIFIED COLORANT FORMED ACCORDING TO EXAMPLE 1 | CI 77492 (and) Alumina (and) Triethoxycaprylylsilane | Modified colorant |
| LUMIRAL | Mica (and) Iron Oxide (and) Titanium Dioxide | Imparts light diffusing properties |
| CM 111 AS | Magnesium Silicate (and)Triethoxycaprylylsilane | Improves spreadability and wear; hydrophobic |

| TRADEMARKED NAMES; AVAILABLE FROM SENSIENT LCW | INCI Name | FUNCTION |
|---|---|---|
| CM 111 | Magnesium Silicate | Improves spreadability and wear |
| MICA 8 AS | Mica (and) Triethoxycaprylylsilane | |
| MODIFIED COLORANT FORMED ACCORDING TO EXAMPLE 8 | CI 77266/D&C Black 2 (and) Alumina (and) Triethoxycaprylylsilane | Modified Colorant |
| MODIFIED COLORANT FORMED ACCORDING TO EXAMPLE 4 | CI 77891 (and) Alumina (and) Triethoxucaprylylsilane | Modified Colorant |
| MODIFIED COLORANT FORMED ACCORDING TO EXAMPLE 2 | CI 22491 (and) Alumina (and) Triethoxycaprylylsilane | Modified Colorant |
| MODIFIED COLORANT FORMED ACCORDING TO EXAMPLE 1 | CI 77492 (and) Alumina (and) Triethoxycaprylylsilane | Modified Colorant |
| COVAPRESS TW 966 | Dimethicone (and) Cetearyl ethylhoxanoate | Oil-free binder |

EXAMPLE 15

Long Lash Mascara Including Modified Colorants

| MATERIALS: | % W/W |
|---|---|
| Phase A | |
| BASE RW 135 | 13.75 |
| DC 200 (350 CST) | 1.37 |
| Phase B | |
| Pure Water | 38.56 |
| Preservative | 0.5 |
| Triethanolamine (85%) | 0.41 |
| THICKAGENT LC | 0.41 |
| Phase C | |
| MODIFIED COLORANT FORMED ACCORDING TO EXAMPLE 8 | 10.00 |
| Phase D | |
| COVACRYL E 14 | 10.00 |
| COVACRYL A 15 | 20.00 |
| Phase E | |
| FIBERLON 102 DC B2 | 5.00 |

METHODS:
1. In a clean stainless steel tank, heat Phase A to about 75° C. with slow stirring.
2. In a separate vessel, dissolve preservative in water and disperse Thickagent LC to make a homogenous gel at cool temperature. Add then Triethanolamine and heat to about 75° C.
3. Add Phase B to Phase A with moderate agitation. Keep on stirring until the product is homogenous. N.B: It is also possible to add A to B, as a function of process equipments.
4. Disperse colorant in a part of base using three-roll mill before adding to the bulk.
5. Add then Covacryl E14 and Covacryl A15, one after another while stirring.
6. Add Fiberlon 102 DC B2 and mix well. Fill into suitable containers.

EXAMPLE 16

Gloss Stick Including Modified Colorants

| MATERIALS: | % W/W |
|---|---|
| Phase A | |
| CLEARWAX | 7.30 |
| COVALIP 94 | 18.00 |
| COVAGLOSS | 2.00 |
| COVACLEAR | 58.40 |
| Phase B | |
| MODIFIED COLORANT FORMED ACCORDING TO EXAMPLE 7 | 0.53 |
| MODIFIED COLORANT FORMED ACCORDING TO EXAMPLE 4 | 1.27 |
| Castor oil | 3.50 |
| Phase C | |
| COVAFLUID AMD | 6.0 |
| Isononyl Isononanoate | 3.0 |
| | 100.00% |

METHODS:
1. Mix Phase A. Grind colorant with three roll-mill in part of Phase A,
2. Add dispersion in Phase A. Maintain temperature at 75° C.,
3. Add Phase C. When homogenous, mold at 75° C.

| TRADEMARKED NAMES; AVAILABLE FROM SENSIENT LCW | INCI Name | FUNCTION |
|---|---|---|
| BASE RW 135 | Synthetic beeswax (and) Carnauba (and) Stearic acid (and) Ceteareth 25 (and) PEG-2 stearate (and) Paraffinum liquidum (and) Hydrogenated coconut oil (and) Cetyl alcohol | Lipophylic mixture for eyeliner |
| THICKAGENT LC | Xanthan gum (and) Hectorite (and) Cellulose | Thickening agent |
| MODIFIED COLORANT FORMED ACCORDING TO EXAMPLE 8 | CI 77266/D&C Black 2 (and) Alumina (and) Triethoxycaprylylsilane | Modified Colorant |
| COVACRYL E 14 | Acrylates copolymer | Film former |
| COVACRYL A15 | Acrylates copolymer | Film former |
| FIBERLON 102 DC B2 | Nylon-6 (and) CI 77266/D&C Black 2 | Lengthens and volumes up eyelashes |

| TRADEMARKED NAMES; AVAILABLE FROM SENSIENT LCW | INCI Name | FUNCTION |
| --- | --- | --- |
| CLEARWAX | Ethylhexyl Hydrostearate (and) Triethylhexyl Trimellitate (and) C30–45 Olefin | Blend of ester and fatty materials |
| COVALIP 94 | Oxokerite (and) Copernicia Cerifera (and) Paraffin (and) Butyl stearate (and) Isopropyl palmitate (and) Paraffinum liquidum (and) Ethylene VA Copolymer (and) Propylparaben | Imparts gloss and long wear. |
| COVAGLOSS | Polyethylene (and) Polybutene (and) Paraffinium liquidum | Soft polymer to impart high gloss |
| MODIFIED COLORANT FORMED ACCORDING TO EXAMPLE 7 | CI 15850 (and) Alumina (and) Triethoxycaprylylsilane | Modified colorant |
| MODIFIED COLORANT FORMED ACCORDING TO EXAMPLE 4 | CI 77891 (and) Alumina (and) Triethoxycparylylsilane | Modified colorant |
| COVACLEAR | Isononyl isonanoate (and) Polybutene (and) Pentaerythrityl Tetraisostearate (and) Isostearyl Alcohol | Provides gloss and hydrophobic film |
| COVAFLUID AMD | Aluminum starch Octenyl succinate | Impact a smooth, velvet touch |

EXAMPLE 17

Eye Shadow Pressed Powder Including Modified Colorants

MATERIALS:

| | % W/W |
| --- | --- |
| Phase A | |
| TALC LCW | 75.00 |
| NYLON 12 | 4.00 |
| CM111 | 5.00 |
| MODIFIED COLORANT FORMED ACCORDING TO EXAMPLE 5 | 2.00 |
| Magnesium Stearate | 5.00 |
| Phase B | |
| COVAPRESS TW 966 | 8.50 |
| Preservative | 0.50 |
| | 100.00% |

METHODS:
1. Blend Phase A using a high speed Osterizer blender.
2. Add Phase B (⅓ at a time) to Phase A and process until homogenous using the blender.
3. Add 2.0 grams of powder to a pan, press at 600 psi with a dwell of 20 seconds.

EXAMPLE 18

Organic Laking on Platelet Alumina

A 25% pure dye lake of D&C Red 7 was prepared via the following procedure. In a 600 mL beaker, 7.5 g of milled D&C Red 7 was mixed with 150 mL of tap water. Mixing was performed with a magnetic stirrer with a baffle added for greater agitation. In a 1-L beaker containing 600 mL of tap water, 22.5 g of ALUSION™ platelet alumina was added. Each slurry was mixed for about 1 hour. The dye slurry was slowly added to the ALUSION™ platelet alumina slurry via a separator funnel to form a third slurry. The pH of the third slurry was between 6.5 and 8.0. The third slurry was stirred for 1.0-1.5 hours and pumped to a filter press. The press cake was then dried at 180 degrees F. (about 82 degrees C.) to form a lake comprising D&C Red 7 and ALUSION™ platelet alumina.

EXAMPLE 19

Organic Laking on Platelet Alumina

A 25% pure dye lake of D&C Red 6 is prepared via the following procedure. In a 600 mL beaker, 7.5 g of milled D&C Red 6 is mixed with 150 mL of tap water. Mixing is performed with a magnetic stirrer with a baffle added for

| TRADEMARKED NAMES; AVAILABLE FROM SENSIENT LCW | INCI Name | FUNCTION |
| --- | --- | --- |
| TALC LCW | Talc | Enhance texture |
| SACCALURONATE CW | Sodium Hyaluronate | Maintains moisture |
| Nylon 12 | Nylon 12 | Provides luxurious feel |
| CM 111 | Magnesium Silicate | Improves spreadability and wear |
| MODIFIED COLORANT FORMED ACCORDING TO EXAMPLE 5 | CI 77288 (and) Alumina (and) Triethoxycaprylylsilane | Modified colorant |
| COVAPEARL OCEAN GREEN 735 AS | CI 77289 (and) CI 77019 (and) Triethoxycaprylylsilane | Pearlescent |
| COVAPRESS TW 966 | Dimethicone (and) Cetearyl ethylhexanoate | Oil free binder | greater agitation. In a 1-L beaker containing 600 mL of tap water, 22.5 g of ALUSION™ platelet alumina is added. Each slurry is mixed for about 1 hour. The dye slurry is slowly added to the ALUSION™ platelet alumina slurry via a separator funnel to form a third slurry. The pH of the third slurry is measured and/or adjusted to be between 6.5 and 8.0. The third slurry is stirred for 1.0-1.5 hours and pumped to a filter press. The press cake is dried at 180 degrees F. (about 82 degrees C.) to form a lake comprising D&C Red 6 and ALUSION™ platelet alumina.

EXAMPLE 20

Carbon Black Wet Processed on Platelet Alumina

A dispersion of carbon black was prepared by adding 22.5 g of carbon black to 300 mL of 22-degree-C. tap water. The dispersion was mixed for about 50 minutes. In a second beaker, 7.5 g of ALUSION™ platelet alumina was combined with 600 mL of tap water and stirred for about one hour. The carbon black dispersion was then slowly added to the ALUSION™ platelet alumina slurry to form a third slurry. There was no bleed of color and the pH of the solution was 7 to 8. The third slurry was filtered through a Buchner filter, and the recovered solids were dried at 180 degrees F. (about 82 degrees C.). The recovered solids had a jet black appearance; however, upon application to the skin, the powder exhibited a metallic effect.

EXAMPLE 21

Surface Treatment of Carbon Black Wet Processed on Platelet Alumina 99 g of a moist modified colorant formed according to Example 3, and 2 g of PEG 12M Dimethicone Copolyol is combined and mixed for 30 seconds. The mixture is heated overnight in an oven at 80 degrees C.

EXAMPLE 22

Dispersion of Surface treated Carbon Black Wet Processed on Platelet Alumina

A modified colorant formed according to Example 4 is dispersed into propylene glycol using a three-roll mill until the final colorant content is about 60%. The resulting dispersion is further incorporated into a mascara formulation.

EXAMPLE 23

Water-Resistant Mascara Including Modified Colorants

| MATERIALS: | |
|---|---|
| | % W/W |
| Phase A | |
| Pure Water | 44.00 |
| COVACRYL RH | 0.10 |
| FUCOMER | 1.00 |
| Methylparaben | 0.30 |
| Phase B | |
| MODIFIED COLORANT FORMED ACCORDING TO EXAMPLE 3 | 6.00 |
| MODIFIED COLORANT FORMED ACCORDING TO EXAMPLE 8 | 6.00 |
| COVABEAD PMMA | 2.00 |
| Phase C | |
| BASE O/W 097 | 6.50 |
| Candellila | 2.50 |
| COVALIP 99 | 1.50 |
| SILAMER | 1.30 |
| Propylparaben | 0.30 |
| Phase D | |
| FIBERLON 102 DC B2 | 0.30 |
| Phase E | |
| Pure Water | 10.00 |
| PPG-17/IPDI/DMPA | 3.00 |
| COVACRYL E14 | 11.00 |
| COVACRYL A15 | 3.50 |

METHODS:
1. Phase A: Heat water in main vessel to 70° C., add Phase A ingredients one by one using a propeller mixer until dissolved.
2. Slowly add Phase B to A, homogenize under high speed mixer until a good dispersion of the color is achieved. Maintain temperature at 70° C.
3. Heat and mix Phase C at 80° C. until homogeneous and maintain at temperature. When ready, add Phase C to main vessel slowly blending with a propeller blade mixer for 15 minutes at 80° C. Add Phase D and mix until homogenous.
4. Cool down main vessel to 40° C. Premix Phase E, slowly add to main vessel while stirring, maintain at 40° C. Cool to appropriate pouring temperature.
Note:
pH = 7.7 (5% mascara in water)

| TRADEMARKED NAMES; AVAILABLE FROM SENSIENT LCW | INCI Name | FUNCTION |
|---|---|---|
| COVACRYL RH | Sodium polyacrylate | Water soluble thickener |
| FUCOMER | Algae extract | Skin and hair moisturizer |
| MODIFIED COLORANT FORMED ACCORDING TO EXAMPLE 3 | CI 77499 (and) Alumina (and) Triethoxycaprylylsilane | Hydrophobic colorant |
| MODIFIED COLORANT FORMED ACCORDING TO EXAMPLE 8 | CI 77266/D&C Black 2 (and) Alumina (and) Nylon 6 (and) Triethoxycaprylylsilane | Lengthens and volume up eyelashes; modified colorant |
| BASE O/W 097 | Ceteareth 25 (and) PEG-2 stearate (and) Paraffinum liquidum (and) Hydrogenated coconut oil (and) Cetyl alcohol (and) Sodium stearate | Self emulsifying and emollient base |
| SILAMER | Phenyl trimethicone (and) Cetyl PEG/PPG-10/1 Dimethicone (and)Polyglyceryl-2-isostearate (and) Hexyl laurate | Self emulsifying base |

| TRADEMARKED NAMES; AVAILABLE FROM SENSIENT LCW | INCI Name | FUNCTION |
| --- | --- | --- |
| FIBERLON 102 DC B2 | Nylon 6 (and) CI 77266/D&C Black 2 | Lengthens and volume-up eyelashes |
| COVARCYL E14 & A15 | Acrylates copolymer | Film former |
| COVABEAD PMMA | Polymethylmethacrylate | Increase smoothness |
| COVALIP 99 | Ozokerite (and) Carnauba (and) Candelilla Cera (and) Paraffin (and) Ricinus communis (and) Butyl Stearate (and) Isopropyl palmitate (and) Paraffinum liquidum (and) Ethylene/VA Copolymer (and) Propylparaben | Provides gloss, long wear and good-pay-off |

EXAMPLE 24

Transparent Soft Two-Way Cake Including Modified Colorants

MATERIALS:

| | % W/W |
| --- | --- |
| Phase A | |
| CM 111 | 57.70 |
| MICA 8 AS | 19.20 |
| Phase B | |
| MODIFIED COLORANT FORMED ACCORDING TO EXAMPLE 8 | 1.90 |
| MODIFIED COLORANT FORMED ACCORDING TO EXAMPLE 4 | 1.90 |
| MODIFIED COLORANT FORMED ACCORDING TO EXAMPLE 2 | 9.60 |
| MODIFIED COLORANT FORMED ACCORDING TO EXAMPLE 1 | 5.80 |
| Phase C | |
| COVAPRESS TW 966 | 3.90 |

METHODS:
1. Mix all the ingredients of Phase A.
2. Mix powder base and colorants then add binder COVAPRESS TW 966 and mix during 30 seconds with a "coffee miller." Compact into suitable godets.

Remark:
octyltriethoxysilane (INCI name: triethoxycaprylylsilane) treatment decreases mixing time.

EXAMPLE 25

Long Lash Mascara Including Modified Colorants

MATERIALS:

| | % W/W |
| --- | --- |
| Phase A | |
| BASE RW 135 | 13.75 |
| DC 200 (350 CST) | 1.37 |
| Phase B | |
| Pure Water | 38.56 |
| Preservative | 0.5 |
| Triethanolamine (85%) | 0.41 |
| THICKAGENT LC | 0.41 |
| Phase C | |
| MODIFIED COLORANT FORMED ACCORDING TO EXAMPLE 8 | 10.00 |
| Phase D | |
| COVACRYL E 14 | 10.00 |
| COVACRYL A 15 | 20.00 |
| Phase E | |
| FIBERLON 102 DC B2 | 5.00 |

METHODS:
1. In a clean stainless steel tank, heat Phase A to about 75° C. with slow stirring.
2. In a separate vessel, dissolve preservative in water and disperse Thickagent LC to make a homogenous gel at a cool temperature. Add then Triethanolamine and heat to about 75° C.
3. Add Phase B to Phase A with moderate agitation. Keep on stirring until the product is homogenous. N.B: It is also possible to add A to B, as a function of process equipment.
4. Disperse colorant in a part of base using three-roll mill before adding to the bulk.
5. Add then Covacryl E14 and Covacryl A15, one after another while stirring.
6. Add Fiberlon 102 DC B2 and mix well. Fill into suitable containers.

| TRADEMARKED NAMES; AVAILABLE FROM SENSIENT LCW | INCI Name | FUNCTION |
| --- | --- | --- |
| CM 111 | Magnesium Silicate | Improves spreadability and wear |
| MICA 8 AS | Mica (and) Triethoxycaprylylsilane | |
| MODIFIED COLORANT FORMED ACCORDING TO EXAMPLE 3 | CI 77266/D&C Black 2 (and) Alumina (and) Triethoxycaprylylsilane | Modified Colorant |
| MODIFIED COLORANT FORMED ACCORDING TO EXAMPLE 4 | CI 77891 (and) Alumina (and) Triethoxucaprylylsilane | Colorant |
| MODIFIED COLORANT FORMED ACCORDING TO EXAMPLE 2 | CI 77491 (and) Alumina (and) Triethoxycaprylylsilane | Colorant |
| MODIFIED COLORANT FORMED ACCORDING TO EXAMPLE 1 | CI 77492 (and) Alumina (and) Triethoxycaprylylsilane | Colorant |
| COVAPRESS TW 966 | Dimethicone (and) Cetearyl ethylhoxanoate | Oil-free binder |

| TRADEMARKED NAMES; AVAILABLE FROM SENSIENT LCW | INCI Name | FUNCTION |
| --- | --- | --- |
| BASE RW 135 | Synthetic beeswax (and) Carnauba (and) Stearic acid (and) Ceteareth 25 (and) PEG-2 stearate (and) Paraffinum liquidum (and) Hydrogenated coconut oil (and) Cetyl alcohol | Lipophylic mixture for eyeliner |
| THICKAGENT LC | Xanthan gum (and) Hectorite (and) Cellulose | Thickening agent |
| MODIFIED COLORANT FORMED ACCORDING TO EXAMPLE 8 | CI 77266/D&C Black 2 (and) Alumina (and) Triethoxycaprylylsilane | Modified Colorant |
| COVACRYL E 14 | Acrylates copolymer | Film former |
| COVACRYL A15 | Acrylates copolymer | Film former |
| FIBERLON 102 DC B2 | Nylon-6 (and) CI 77266/D&C Black 2 | Lengthens and volumes up eyelashes |

EXAMPLE 26

Gloss Stick Including Modified Colorants

| MATERIALS: | % W/W |
| --- | --- |
| Phase A | |
| CLEARWAX | 7.30 |
| COVALIP 94 | 18.00 |
| COVAGLOSS | 2.00 |
| COVACLEAR | 58.40 |
| Phase B | |
| MODIFIED COLORANT FORMED ACCORDING TO EXAMPLE 6 | 0.53 |
| MODIFIED COLORANT FORMED ACCORDING TO EXAMPLE 4 | 1.27 |
| Castor oil | 3.50 |
| Phase C | |
| COVAFLUID AMD | 6.0 |
| Isononyl Isononanoate | 3.0 |
| | 100.00% |

METHODS:
1. Grind colorant (Phase B) with three roll-mill in part of Phase A,
2. Add dispersion in Phase A. Maintain temperature at 75° C.,
3. Add Phase C, when homogenous, mold at 75° C.

EXAMPLE 27

Transfer-Resistant Moisture Lipstick

| MATERIALS: | % W/W |
| --- | --- |
| Phase A | |
| SILAMER | 11.50 |
| COVABEAD LH85 | 5.00 |
| Dow Corning AMC-C30 | 5.00 |
| Dow Corning 2503 | 2.50 |
| SQUATOL S | 5.00 |
| Microcrystalline Wax #118P | 4.80 |
| Ozokerite Wax #116 | 1.20 |
| COVABEES S99 | 6.00 |
| Propylparaben | 0.10 |
| Phase B | |
| Isopropyl Myristate (IPM) | 4.40 |
| MODIFIED COLORANT FORMED ACCORDING TO EXAMPLE 6 | 6.00 |
| COVAPEARL SILVER 939 AS | 1.40 |
| NOIR COVAMIC W9364 | 0.10 |
| Phase C | |
| Dow Corning 245 | 2.00 |

| TRADEMARKED NAMES; AVAILABLE FROM SENSIENT LCW | INCI Name | FUNCTION |
| --- | --- | --- |
| CLEARWAX | Ethylhexyl Hydrostearate (and) Triethylhexyl Trimellitate (and) C30–45 Olefin | Blend of ester and fatty materials |
| COVALIP 94 | Oxokerite (and) Copernicia Cerifera (and) Paraffin (and) Butyl stearate (and) Isopropyl palmitate (and) Paraffinum liquidum (and) Ethylene VA Copolymer (and) Propylparaben | Imparts gloss and long wear. |
| COVAGLOSS | Polyethylene (and) Polybutene (and) Paraffinium liquidum | Soft polymer to impart high gloss |
| MODIFIED COLORANT FORMED ACCORDING TO EXAMPLE 6 | CI 15850 (and) Alumina (and) Triethoxycaprylylsilane | Modified colorant |
| MODIFIED COLORANT FORMED ACCORDING TO EXAMPLE 4 | CI 77891 (and) Alumina (and) Triethoxycparylylsilane | Colorant |
| COVACLEAR | Isononyl isonanoate (and) Polybutene (and) Pentaerythrityl Tetraisostearate (and) Isostearyl Alcohol | Provides gloss and hydrophobic film |
| COVAFLUID AMD | Aluminum starch Octenyl succinate | Impact a smooth, velvet touch |

-continued

| MATERIALS: | % W/W |
|---|---|
| Phase D | |
| Pure Water | 22.50 |
| FRUCTOSOL | 2.50 |
| COVACRYL E14 | 10.00 |
| Polyglyceryl-3 Laurate | 2.00 |
| Propylene Glycol | 3.00 |
| SUBMICA E | 2.00 |
| Phase E | |
| Dow Corning 245 | 3.00 |
| | 100.00% |

METHODS:
1. Mix and heat Phase A to 90° C. until dissolved.
2. Mix Phase B and C, add to Phase A and mix, bring down temperature to 80° C.
3. Pre-mix Phase D and then add to bulk. Continue mixing and maintain temperature.
4. Add Phase E until homogenous. Pour into a lipstick mold at 75° C.–78° C.

| TRADEMARKED NAMES; AVAILABLE FROM SENSIENT LCW | INCI Name | FUNCTION |
|---|---|---|
| SILAMER | Phenyl trimethicone (and) Cetyl PEG/PPG-10/1 Dimethicone (and) Polyglyceryl-2-isostearate (and) Hexyl Laurate | Non-ionic self-emulsifying base |
| COVABEAD LH85 | Methylmethacrylate cross polymer | Strong capacity of oil and water absorption |
| COVABEES S99 | Synthetic beeswax | High melting point wax |
| SQUATOL S | Hydrogenated polyisobutene | Gives a coherent film that protects the skin |
| MODIFIED COLORANT FORMED ACCORDING TO EXAMPLE 6 | CI 15850 (and) Alumina (and) Triethoxycaprylylsilane | Modified Colorant |
| FRUCTOSOL | Cichorium Intybus | Moisturizes the skin |
| COVACRYL E14 | Acrylates copolymer | Film former |
| COVAPEARL SILVER 939 AS | CI 77891 (and) CI 77019 (and) Triethoxycaprylylsilane | Pearlescent |
| SUBMICA E | Mica | High swelling capacity in water |

EXAMPLE 28

Red Iron Oxide Dry Blended with Bismuth Oxychloride 20 g of red iron oxide (Unipure LC 381 obtainable from Sensient LCW), 79 g of bismuth oxychloride, 1 g of deionized water and 2 g of octyltriethoxysilane (INCI name triethoxycaprylylsilane) are mixed for 30 seconds. The mixture is then heated overnight in an 80° C. oven. The feel on the skin is very soft, and the payoff has a very high luster. The percent loss on drying is 0.14%, and the product is hydrophobic.

While the present invention has now been described and exemplified with some specificity, those skilled in the art will appreciate the various modifications, including variations, additions and omissions, that may be made in what has been described. All patents, publications and references cited herein are hereby fully incorporated by reference. In case of conflict between the present disclosure and incorporated patents, publications and references, the present disclosure should control.

What is claimed is:

1. A modified colorant comprising platelet alumina, a colorant and a surface treatment, wherein the colorant is adhered randomly to a surface of the platelet alumina by the surface treatment and partially coats the platelet alumina.

2. The modified colorant of claim 1, wherein the platelet alumina has a surface area and the colorant is adhered to about 5% to 90% of the surface area.

3. The modified colorant of claim 1, wherein the colorant comprises a pigment.

4. The modified colorant of claim 1, wherein the surface treatment comprises a material selected from aluminum laurate, aluminum stearate, an amino acid, chitin, collagen, fluorochemical, lecithin, metal soap, natural wax, polyacrylate, polyethylene, silicone, silane, titanatate ester, urethane, dimethicone, perfluoropolymethylisopropyl ether, styrene acrylates copolymer, magnesium myristate, lauroyl lysine and a combination thereof.

5. The modified colorant of claim 1, wherein the surface treatment comprises a material selected from methicone, triethoxycaprylylsilane, trimethoxycaprylylsilane, dimethicone copolyol and a combination thereof.

6. A method of making the modified colorant of claim 1 comprising:
 (a) dry blending the platelet alumina and the colorant to form a dry blend; and
 (b) adding a surface treatment to the dry blend to form the modified colorant.

7. The modified colorant of claim 1, wherein the colorant has a weight percentage of about 15% to about 60% of the total combined weight percentage of the colorant and the platelet alumina.

8. The modified colorant of claim 7, wherein the colorant has a weight percentage of about 15% to about 35% of the total combined weight percentage of the colorant and the platelet alumina.

9. The modified colorant of claim 7, wherein the colorant has a weight percentage of about 35% to about 55% of the total combined weight percentage of the colorant and the platelet alumina.

10. A cosmetic product comprising the modified colorant of claim 1.

11. A modified colorant comprising platelet alumina having a surface area coated with a colorant, wherein the colorant is adhered randomly to the platelet alumina with a surface treatment, coats from about 5% to about 99% of the surface area of the platelet alumina, and does not completely coat the platelet alumina, and wherein the modified colorant exhibits increased burnishing when compared with platelet alumina completely coated with colorant.

12. The modified colorant of claim 11, wherein the colorant comprises a pigment laked onto the platelet alumina.

13. A cosmetic product comprising the modified colorant of claim 11.

14. A modified colorant comprising platelet alumina coated with a colorant, wherein the platelet alumina comprises an upper surface and a lower surface separated by an edge, wherein the colorant is adhered randomly to the platelet alumina by a surface treatment and the edge of the platelet alumina is substantially free of colorant.

15. The modified colorant of claim 14, wherein the platelet alumina has a surface area and the colorant is adhered to from about 5% to about 90% of the surface area.

16. The modified colorant of claim 1, wherein the modified colorant exhibits a metallic sheen when burnished.

17. The modified colorant of claim 1, where in the colorant is formed by mixing the platelet alumina with the colorant and the surface treatment.

18. The modified colorant of claim 1, wherein the colorant is randomly adhered to the platelet alumina by:
   (a) dry blending the platelet alumina and the colorant to form a dry blend; and
   (b) adding the surface treatment to the dry blend to form the modified colorant.

19. The modified colorant of claim 11, where in the colorant is formed by mixing the platelet alumina with the colorant and the surface treatment.

20. The modified colorant of claim 11, wherein the colorant is randomly adhered to the platelet alumina by
   (a) dry blending the platelet alumina and the colorant to form a dry blend; and
   (b) adding the surface treatment to the dry blend to form the modified colorant.

21. The modified colorant of claim 14, wherein the colorant is formed by mixing the platelet alumina with the colorant and the surface treatment.

22. The modified colorant of claim 14, wherein the colorant is randomly adhered to the platelet alumina by
   (a) dry blending the platelet alumina and the colorant to form a dry blend; and
   (b) adding the surface treatment to the dry blend to form the modified colorant.

* * * * *